US008663666B2

(12) United States Patent
Morita et al.

(10) Patent No.: US 8,663,666 B2
(45) Date of Patent: Mar. 4, 2014

(54) WATER BASED LIQUID MAKEUP COSMETIC

(75) Inventors: Masaaki Morita, Fujioka (JP); Hiroshi Satoh, Fujioka (JP)

(73) Assignee: Mitsubishi Pencil Company, Limited, Shinagawa-Ku, Tokyo (JP)

( * ) Notice: Subject to any disclaimer, the term of this patent is extended or adjusted under 35 U.S.C. 154(b) by 540 days.

(21) Appl. No.: 12/296,731

(22) PCT Filed: Apr. 17, 2007

(86) PCT No.: PCT/JP2007/058333
§ 371 (c)(1), (2), (4) Date: Oct. 10, 2008

(87) PCT Pub. No.: WO2007/123115
PCT Pub. Date: Nov. 1, 2007

(65) Prior Publication Data

US 2009/0175813 A1 Jul. 9, 2009

(30) Foreign Application Priority Data

Apr. 17, 2006 (JP) ................................ 2006-113608

(51) Int. Cl.
*A61Q 1/10* (2006.01)

(52) U.S. Cl.
USPC ........................ 424/401; 424/70.6; 424/70.16

(58) Field of Classification Search
None
See application file for complete search history.

(56) References Cited

U.S. PATENT DOCUMENTS

| | | | | |
|---|---|---|---|---|
| 5,228,912 | A | 7/1993 | Herget et al. | |
| 6,235,293 | B1 * | 5/2001 | De La Poterie et al. | 424/401 |
| 6,294,158 | B1 * | 9/2001 | Dupuis | 424/70.1 |
| 6,440,430 | B1 | 8/2002 | Bara et al. | |
| 6,506,376 | B2 | 1/2003 | Sato | |
| 2002/0006422 | A1 | 1/2002 | Koda et al. | |
| 2002/0051756 | A1 * | 5/2002 | Sato | 424/61 |
| 2003/0086887 | A1 * | 5/2003 | De La Poterie et al. | 424/70.11 |
| 2003/0138469 | A1 | 7/2003 | Koda et al. | |
| 2004/0042994 | A1 | 3/2004 | Dausch et al. | |
| 2005/0002881 | A1 * | 1/2005 | Aota | 424/63 |
| 2008/0312395 | A1 | 12/2008 | Muller et al. | |

FOREIGN PATENT DOCUMENTS

| | | | |
|---|---|---|---|
| EP | 0103199 | B1 * | 3/1988 |
| JP | 61-100508 | | 5/1986 |
| JP | 4-230207 | A | 8/1992 |
| JP | 5-171058 | A | 7/1993 |
| JP | 7-030263 | B2 | 1/1995 |
| JP | 7-69831 | A | 3/1995 |
| JP | 8-040829 | A | 2/1996 |
| JP | 8-040832 | A | 2/1996 |
| JP | 9-151115 | A | 6/1997 |
| JP | 2672908 | B2 | 7/1997 |
| JP | 9-267068 | A | 10/1997 |
| JP | 10-085037 | A | 4/1998 |
| JP | 11-302126 | A | 11/1999 |
| JP | 11-322533 | A | 11/1999 |
| JP | 2000-247833 | A | 9/2000 |
| JP | 2001-254027 | A | 9/2001 |
| JP | 2002-3335 | A | 1/2002 |
| JP | 2002-047140 | A | 2/2002 |
| JP | 2003-231614 | A | 8/2003 |
| JP | 2004-514000 | A | 5/2004 |
| JP | 2005-015344 | | 1/2005 |
| JP | 2005-205809 | A | 8/2005 |
| JP | 2005-527548 | A | 9/2005 |
| JP | 2006-069965 | A | 3/2006 |
| WO | WO 2005/068520 | A1 | 7/2005 |

OTHER PUBLICATIONS

Mizutani et al. Machine Translation of JP 11302126. Pub. Nov. 2, 1999.*
Notification of Transmittal of Translation of the International Preliminary Report on Patentability (Form PCT/IB/338), International Preliminary Report on Patentability (Form PCT/IB/373), Written Opinion of the International Search Authority (Form PCT/ISA/237) mailed in corresponding International Patent Application No. PCT/JP2007/058333, Apr. 17, 2007, The International Bureau of WIPO, Geneva, CH.
International Search Report for corresponding application No. PCT/JP2007/058333, completed Jul. 4, 2007.
Extended European Search Report, including the supplementary European Search Report and the European Search Opinion, issued Dec. 10, 2012, in corresponding European Applciation No. 07741769.9.
New Cosmetic Science, Nansando Co., Ltd., Jan. 18, 2001, second edition, p. 106.
Fragrance Journal, vol. 20, No. 10, p. 99, Oct. 15, 1992.

* cited by examiner

*Primary Examiner* — Jyothsna Venkat
(74) *Attorney, Agent, or Firm* — Buchanan Ingersoll & Rooney PC

(57) ABSTRACT

Provided is a water based liquid makeup cosmetic which is filled in an applicator for a liquid cosmetic equipped with a brush-like coating part to be suitably used for making up, particularly a water based liquid makeup cosmetic which is suited for making up around eyes, and in order to obtain the cosmetic, assumed is a formation comprising at least a tabular pigment, a pigment dispersant, a coating film-forming agent, 0.001 to 0.5 mass % of a surfactant and water and further comprising a spherical powder.
According to the formation for a water based liquid makeup cosmetic, obtained is a water based liquid makeup cosmetic which makes it easy to rehomogenize (redisperse) the cosmetic by slightly shaking even after turned into an uneven state with standing still during storage and which makes fine lines liable to be drawn and is excellent in a water resistant fixing performance.

5 Claims, 1 Drawing Sheet

WATER BASED LIQUID MAKEUP COSMETIC

TECHNICAL FIELD

The present invention relates to a water based liquid makeup cosmetic, more specifically to a water based liquid makeup cosmetic which is filled in an applicator for a liquid cosmetic equipped with a brush-like coating part to be suitably used for making up, particularly a water based liquid makeup cosmetic which is suited for making up around eyes.

BACKGROUND ART

A large variety of blend compositions has so far been known as a water based eye makeup cosmetic.

The present applicants have proposed a water based eye makeup cosmetic (refer to, for example, patent document 1) comprising a so-called pearl pigment such as mica, titanium dioxide coated mica as a blend composition, and technology on a settling property of the above tabular particles and redispersibility of the settled particles has been disclosed at the same time.

However, an eyeliner liquid cosmetic of a fine pearl color disclosed in patent document 1 is restricted to an eyeliner liquid cosmetic which has a viscosity value falling in a prescribed range regulated by a shear rate for stabilization and which is blended with a stabilizing agent such as hydrogenated lecithin and a dispersant such as polyethylene glycol fatty acid ester.

Fine eyelines can be drawn with the above eyeliner liquid cosmetic, but observed is a defect that the blended components (particularly the tabular pigment having a large particle diameter described above) settle down with the passage of time in storage to form a hard cake. In addition thereto, defects that narrow lines are less liable to be drawn due to that the tabular pigment having a large particle diameter is blended and that the water resistant fixing performance is inferior are not yet completely solved in the above eyeliner liquid cosmetic.

On the other hand, a tabular pigment which is improved in dispersibility is proposed (refer to, for example, patent document 2). However, the tabular pigment disclosed in patent document 2 is a tabular pigment coated with a polymer such as polyacrylate, and a particle diameter thereof is not specifically studied.

A liquid makeup cosmetic which has a good spreading property and is excellent in use feeling is proposed as a prior art filed by the present applicant (refer to, for example, patent document 3). However, in the cosmetic described in patent document 3, specific originality is not shown to a coloring agent blended, and the liquid makeup cosmetic described therein comprises an acryl-silicone base graft copolymer, a spherical fine particle powder and a low boiling silicone oil, whereby it is characterized in that a spreading property and smooth use feeling are obtained. Further, use of the tabular particles which is characterized in the present invention is by no means referred to in the patent document 3.

Further, provided is a powder cosmetic which contains a tabular powder subjected to surface treatment and a monodispersed spherical powder having an average particle diameter of 0.01 to 2 μm and which is excellent in smooth feeling in use (refer to, for example, patent document 4). Powder cosmetics characterized by having, as is the case with the above, smooth feeling are known as well (refer to, for example, patent documents 5 to 7). However, they are powder cosmetics or non-water based powders in all cases, and not only they are cosmetics belonging to a different category from that of the water based liquid makeup cosmetic of the present invention, but also technology on redispersibility of the tabular particles which is characterized in the present invention is neither described nor suggested therein.

Also, known is processed colored powder prepared by electrostatically adsorbing a pigment on a resin powder of nylon, polyethylene, polystyrene, polymethyl methacrylate, silicone or the like and driving it into the resin powder by mechanical impact force (refer to, for example, patent document 8). In the patent document 8, a water based eyeliner containing 15 parts of the processed colored powder described above is provided in Application Example 5. However, technology on redispersibility of the tabular particles which are characterized in the present invention is not found to be either described or suggested in document 8 including the above Application Example 5.

Further, an emulsion (refer to, for example, patent document 9) used for modifying, as is the case with patent document 8, powder is also known, but particularly redispersibility of the tabular particles which is intended in the present invention is neither described nor suggested therein.

Patent document 1: Japanese Patent Application Laid-Open No. 2000-247833 (claims, examples and others)
Patent document 2: Japanese Patent Application Laid-Open Hei 05 No. 171058 (claims, examples and others)
Patent document 3: Japanese Patent Application Laid-Open No. 2002-47140 (claims, examples and others)
Patent document 4: Japanese Patent No. 2672908 (claims, examples and others)
Patent document 5: Japanese Patent Application Laid-Open Hei 04 No. 230207 (claims, examples and others)
Patent document 6: Japanese Patent Application Laid-Open Hei 08 No. 40829 (claims, examples and others)
Patent document 7: Japanese Patent Application Laid-Open No. 2001-254027 (claims, examples and others)
Patent document 8: Japanese Examined Patent Application Publication Hei 07 No. 30263 (claims, examples and others)
Patent document 9: Japanese Translation of PCT International Application No. 2005-527548 (claims, examples and others)

DISCLOSURE OF THE INVENTION

Problems to be Solved by the Invention

An object of the present invention is to provide a water based liquid makeup cosmetic containing a tabular pigment, wherein it is liable to draw fine lines and is excellent in a water resistant fixing performance; tabular coarse particles contained therein as an active ingredient is less liable to settle down; and the cosmetic can be evenly redispersed by slightly shaking even when it is not used for a while.

Means for Solving the Problems

The present inventors have repeated intensive researches in order to achieve the object described above, and the present invention has come to be completed.

That is, the present invention comprises the following items (1) to (8).

(1) A water based liquid makeup cosmetic having a viscosity of 50 to 250 mPa·s and containing at least a tabular pigment, a pigment dispersant, a coating film-forming agent, 0.001 to 0.5 mass % of a surfactant and water, wherein it further contains a spherical powder.

(2) The water based liquid makeup cosmetic as described in the above item (1), wherein the tabular pigment is at least one pigment selected from the group consisting of mica, titanium dioxide coated mica, a metal or metal oxide-coated glass flake, an aluminum-coated polyester film and an aluminum powder pigment.
(3) The water based liquid makeup cosmetic as described in the above item (1) or (2), wherein the spherical powder is a spherical powder comprising at least one of spherical silica particles, spherical mica particles, spherical nylon particles, spherical acrylic resin particles and spherical polystyrene particles.
(4) The water based liquid makeup cosmetic as described in any one of the above items (1) to (3), wherein the pigment dispersant is a homopolymer or a copolymer prepared from raw material monomers comprising at least one compound selected from acrylic acid, methacrylic acid and alkyl (C1 to C4 and C8) esters thereof.
(5) The water based liquid makeup cosmetic as described in any one of the above items (1) to (4), wherein the coating film-forming agent is an emulsion of a homopolymer or a copolymer prepared from at least one monomer selected from acrylic acid, methacrylic acid and alkyl (C1 to C4 and C8) esters thereof.
(6) A water based liquid eye-makeup cosmetic comprising the water based liquid eye-makeup cosmetic as described in any one of the above items (1) to (5), wherein it is used for making up around eyes.
(7) An eyeliner prepared by filling the water based liquid makeup cosmetic as described in the above item (6) directly into a storing part of an applicator for a liquid cosmetic equipped with a brush-like coating part.
(8) The eyeliner as described in the above item (7), wherein at least one stirrer is accommodated in the storing part of the applicator for a liquid cosmetic.

Effects of the Invention

According to the present invention, provided is a water based liquid makeup cosmetic which is reduced in quick settling of a tabular pigment comprising tabular coarse particles liable to settle down and makes it possible to rehomogenize (redisperse) the cosmetic causing precipitation during storage (standing still) by slightly shaking and which makes fine lines liable to be drawn and is excellent in a water resistant fixing performance.

EXPLANATION OF REFERENCE NUMERALS AND LETTERS

Figure 1:
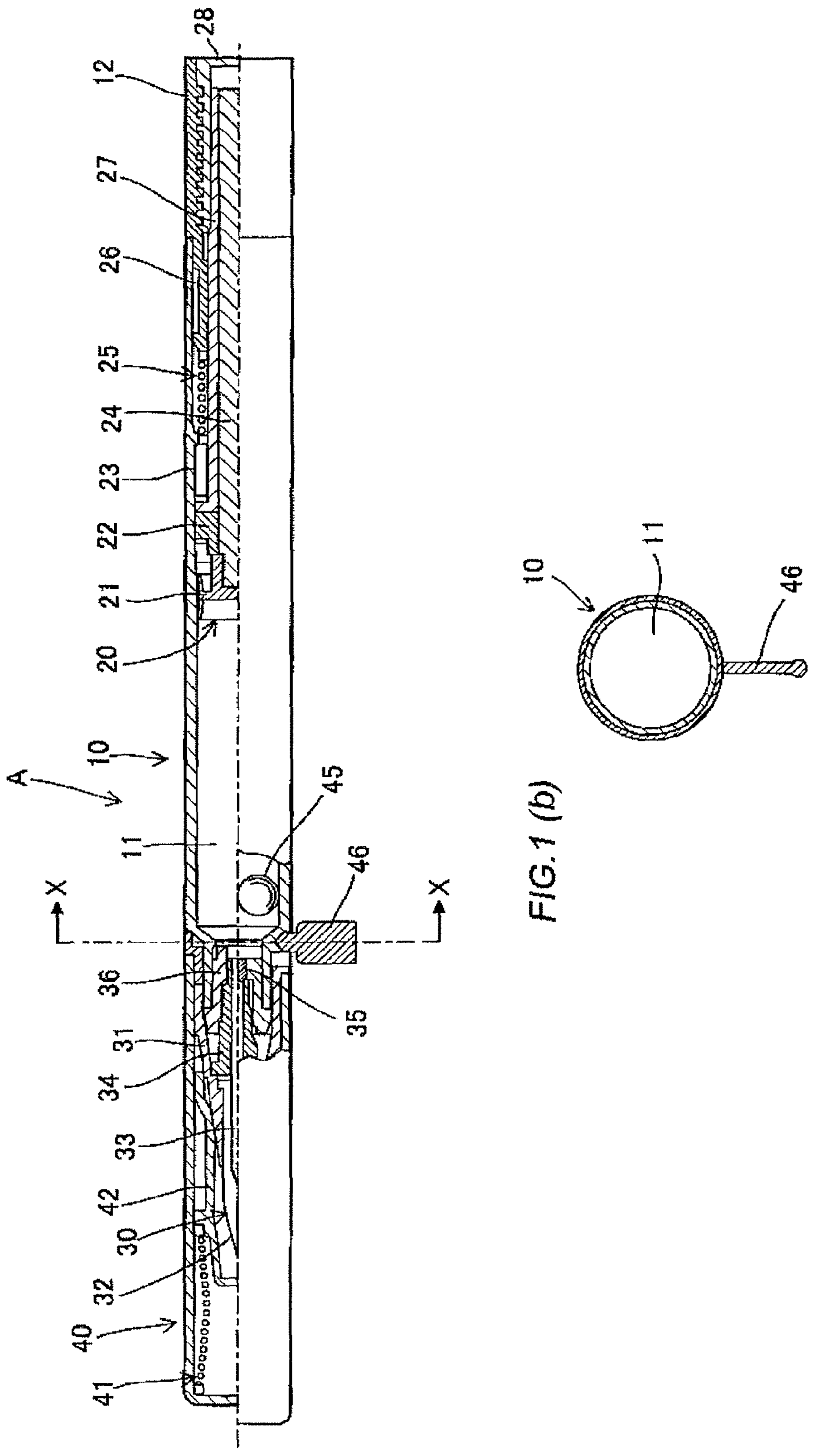
FIG. 1 shows one example of an eyeliner which is a specific example of a cosmetic applicator filled with the water based liquid makeup cosmetic of the present invention; (a) is a partial vertical cross-sectional drawing of the whole body; and (b) is an x-x cross-sectional drawing of (a).

A Eyeliner
10 Main body part
20 Piston mechanism
30 Coating mechanism
40 Cap member

BEST MODE FOR CARRYING OUT THE INVENTION

The embodiment of the present invention shall be explained below in details.

The water based liquid makeup cosmetic of the present invention is a water based liquid makeup cosmetic having a viscosity of 50 to 250 mPa·s and containing at least a tabular pigment, a pigment dispersant, a coating film-forming agent, 0.001 to 0.05 mass % of a surfactant and water, wherein it further contains a spherical powder.

The tabular pigment used in the water based liquid makeup cosmetic of the present invention is a pearl pigment, and the pearl pigment is highly safe to a human body. The specific examples thereof include mica, titanium dioxide coated mica, bismuth oxychloride, carmine•titanium dioxide coated mica, carmine•prussian blue•titanium dioxide coated mica, black iron oxide, black iron oxide•titanium dioxide coated mica, prussian blue coated mica, prussian blue•titanium dioxide coated mica, red iron oxide coated mica, red iron oxide•titanium dioxide coated mica, red iron oxide•carmine•titanium dioxide coated mica, red iron oxide•black iron oxide•titanium dioxide coated mica, red iron oxide•prussian blue•titanium dioxide coated mica, red iron oxide•iron oxide•prussian blue•titanium dioxide coated mica, $N_\epsilon$-lauroyl-L-lysin coated mica and the like.

The pearl pigments each may be used alone or in combination of two or more kinds thereof.

The smaller the particle diameter of the pearl pigment used in the water based liquid makeup cosmetic of the present invention is, the more the pearl pigment loses gloss feeling and brightness feeling, and therefore that is not preferred. On the other hand, the larger the particle diameter thereof is, the more the weight of the particle is increased, and it is more difficult to control settling thereof. From this point of view, the pearl pigment having an average particle diameter of 5 to 150 μm is suited.

The specific examples of the pearl pigment used for the tabular pigment include, for example, a Metashine series manufactured by Nippon Sheet Glass Co., Ltd., a Crystal Color series manufactured by Daiya Kogyo Co., Ltd., a Fine Flake series manufactured by Katani Sangyo Co., Ltd. and the like. Among them, Metashine having an average particle diameter of 20 to 100 μm is most suited.

A content of the above tabular pigments is preferably 5 to 25 mass % based on the total mass of the water based liquid makeup cosmetic in order to obtain the good drawn lines, the good coating performance and the good use characteristics.

In the water based liquid makeup cosmetic of the present invention, not only the pearl pigment can be blended alone as the tabular pigment, but also the pearl pigment can be blended in combination with inorganic pigments.

Capable of being used as the inorganic pigments are, for example, black iron oxide, yellow iron oxide, chromium oxide, ultramarine blue, prussian blue, zinc oxide, aluminum oxide, silicon dioxide, titanium oxide, magnesium oxide, chromium hydroxide, calcium carbonate, titanium yellow, red iron oxide and the like. A blending amount of the inorganic pigments shall not specifically be restricted, and an optional amount thereof can suitably be blended within a viscosity range of the water based liquid makeup cosmetic of the present invention. In addition to the pearl pigments and the inorganic pigments each described above, other pearl pigments excluding the pearl pigments described above (for example, fish scale flake, $N_\epsilon$-lauroyl-L-lysin-coated talc and the like), organic pigments and other various dyes can be used if necessary.

The spherical powder used in the present invention is used as a dispersion auxiliary agent, and the spherical powder is selected, for example, from at least one of spherical silica particles, spherical mica particles, spherical nylon particles, spherical acrylic resin particles and spherical polystyrene particles.

To be specific, capable of being used are cross-linked or non-cross-linked acryl resin monodispersed particles, cross-linked or non-cross-linked polystyrene monodispersed particles and spherical bead polymers comprising methyl methacrylate as a principal component. They include Jurymer MB-1, MB-S, MB-20 and MB-1P (manufactured by Nihon Junyaku Co., Ltd.), Techpolymer MB-C series, MBP series, MBX-C series and ACX series (manufactured by Sekisui Plastics Co., Ltd.), Ganz Pearl series and Chemisnow series (manufactured by Soken Chemical & Engineering Co., Ltd.), Matsumoto Microsphere M series (manufactured by Matsumoto Yushi-Seiyaku Co., Ltd.) and the like. Silica Microbeads series (manufactured by Catalysts & Chemicals Ind. Co., Ltd.), Sunsphere series (manufactured by Asahi Glass Co., Ltd.) and the like can be used as spherical silica.

A size (average particle diameter) of the spherical powder used is, though depending on the kinds of an applicator filled with the water based liquid makeup cosmetic and the tabular pigment added, preferably 3 μm or less, more preferably 0.1 to 0.8 μm in a case where a coating part of the applicator is brush-like.

A content of the spherical powder is preferably 0.5 to 5 mass % based on the total mass of the water based liquid makeup cosmetic in order to reduce (less liable to settle down) a settling rate of the tabular pigment and obtain the good redispersibility.

In the water based liquid makeup cosmetic of the present invention, a homopolymer or a copolymer prepared from raw material monomers comprising at least one compound selected from acrylic acid, methacrylic acid and alkyl (C1 to C4 and C8) esters thereof is used as the pigment dispersant for the tabular pigment described above. The homopolymer or copolymer has preferably an acid residue as a side chain in a repetitive structure thereof, and acrylic resins and alkyl acrylate copolymers which can be dissolved in water by neutralization are preferred. A copolymer (shown by the following formula) prepared from a mixture comprising tert-butyl acrylate, ethyl acrylate and methacrylic acid is shown as an example of the particularly preferred alkyl acrylate copolymers, and a commercially available product thereof includes Luvimer 100P (manufactured by BASF AG.).

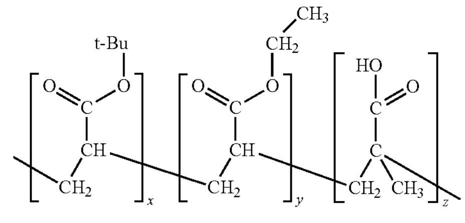

(wherein x, y and z each are an integer of 1 or more, and a relation of x+y+z=190 to 230 is satisfied).

For dissolving the polymer in water by neutralization, capable of being suitably used are organic basic compounds such as 2-amino-2-methyl-1-propanol, 2-amino-2-methyl-1,3-propanediol, L-arginine and inorganic basic compounds such as aqueous ammonia, sodium hydroxide which can be paired with organic acid residues having a free bulky organic group to form salts. Among them, the particularly preferred basic compound is 2-amino-2-methyl-1-propanol.

In the water based liquid makeup cosmetic of the present invention, capable of being used as the above dispersant is an aqueous solution prepared by reacting the basic compounds with the homopolymer or copolymer described above in the equivalent amount to form a polymer structure having a salt and then adding thereto refined water of a minimum amount necessary for dissolving it. In Table 1 and Table 2 described later, a content of the dispersant shows an amount (mass % based on the total mass of the water based liquid makeup cosmetic) calculated based on a mass of the resin content contained in the dispersant.

In the water based liquid makeup cosmetic of the present invention, a content of the above pigment dispersant is preferably 0.5 to 5 mass %, more preferably 2 to 4 mass % based on the total mass of the water based liquid makeup cosmetic.

If the content of the pigment dispersant is less than 0.5 mass %, dispersion stability of the tabular pigment is insufficient. On the other hand, if the pigment dispersant is contained in excess of 5 mass %, the viscosity grows too high, and the dispersion stability is not improved, so that it is not economical.

Used as the coating film-forming agent used in the present invention is an emulsion (in both cases of a homopolymer and a copolymer, a water suspension obtained by emulsion-polymerizing monomers in water as a polymerization solvent) of a homopolymer (provided that a homopolymer comprising only polystyrene is excluded) or a copolymer prepared from raw material monomers comprising at least one compound selected from acrylic acid, methacrylic acid or alkyl (C1 to C4 and C8) esters thereof and styrene.

In the present invention, an emulsion of a homopolymer or a copolymer prepared from at least one monomer selected from acrylic acid, methacrylic acid and alkyl (C1 to C4 and C8) esters thereof can suitably be used as the emulsion of the coating film-forming agent.

A content of the coating film-forming agent is preferably 2 to 15 mass % in terms of a solid based on the total mass of the liquid cosmetic. If the content of the coating film-forming agent is less than 2 mass %, the water resistance is inferior. On the other hand, if it exceeds 15 mass %, the coating part of the applicator is likely to dry to make coating impossible.

A suited amount of a surfactant is added in order to stabilize the emulsion of the coating film-forming agent. In this case, surfactants of any kinds of a nonionic base, a cationic base and an anionic base can be used as the surfactant. To be specific, it includes at least one of lecithin, propylene glycol fatty acid esters, glycerin fatty acid esters, polyglycerin fatty acid esters, polyoxyethylene alkyl ethers, polyoxyethylene polyoxypropylene alkyl ethers, polyoxyethylene alkyl ether phosphoric acid esters, polyethylene glycol fatty acid ester•alkyl sulfate (sulfonic acid esters), polyoxyethylene alkyl ether sulfate and the like.

When an emulsion is added as the coating film-forming agent, a sum of the amount of the surfactant including that contained in the emulsion is 0.001 to 0.5 mass % based on the total liquid cosmetic.

If an amount of the surfactant is added in excess of 0.5 mass %, the water resistance is inferior, and the satisfactory fixing strength can not be obtained. On the other hand, if the surfactant is added in an amount of less than 0.001 mass %, an addition effect thereof is not obtained.

The water based liquid makeup cosmetic of the present invention may contain a chelating agent, a moisturizing agent, a thickener, an antiseptic agent and the like which are usually used for water based liquid makeup cosmetics in addition to the tabular pigment, the pigment dispersant, the coating film-forming agent, the surfactant and the spherical powder as long as the effects of the present invention are not damaged, and the balance is adjusted by water such as refined water, ion-exchanged water.

In the water based liquid makeup cosmetic of the present invention, a viscosity (EMD type viscometer, 25° C., shearing rate: 76.8 $s^{-1}$) is controlled to a range of 50 to 250 mPa·s from the viewpoints of settling control and redispersibility of the tabular pigment and the coating performance.

If the viscosity is less than 50 mPa·s, the tabular pigment is notably settled down and is inferior in redispersibility, and therefore it is not preferred. On the other hand, if it exceeds 250 mPa·s, the viscosity is too high, so that the coating performance of the liquid cosmetic is inferior. In particular, when it is used as an eyeliner cosmetic, fine lines can not be drawn, and therefore that range is not preferred.

In the water based liquid makeup cosmetic of the present invention constituted in the manner described above, though the tabular pigment which forms tabular coarse particles is used, the tabular coarse particles are less liable to be settled down, and even when they have been settled down, the cosmetic can evenly be redispersed by slight force, so that it is no problem to employ a method in which the cosmetic is stored directly in a container for storing a cosmetic. Accordingly, when the water based liquid makeup cosmetic of the present invention is stored directly in the container, a stirrer is not necessarily required to be put therein, and it becomes possible to constitute the container itself for the cosmetic in a small or narrow form.

Also, if at least one small and light stirrer which is commensurate with the container is put therein, it becomes possible to evenly redisperse the cosmetic by force thereof, and therefore the cosmetic can more suitably be used.

Further, the water based liquid makeup cosmetic of the present invention can be a water based liquid makeup cosmetic which is suited particularly for eye makeup around eyes.

A structure of a cosmetic applicator which is filled with the water based liquid makeup cosmetic of the present invention shall not specifically be restricted, and it includes, for example, an eyeliner shown in FIG. 1 which is a specific example of the cosmetic applicator which is filled with the water based liquid makeup cosmetic of the present invention.

The eyeliner A is equipped, as shown in FIG. 1, with a main body part 10 having a storing part 11 of an applicator for a liquid cosmetic in the inside, a rotating member 12 mounted at a rear part of the main body part 10, a piston mechanism 20 for pushing out an eyeliner cosmetic liquid which is the water based liquid makeup cosmetic of the present invention and which is filled directly into the storing part 11 toward a coating mechanism 30 at a front part by rotation of the rotating member 12, and a cap member 40.

The piston mechanism 20 is constituted from a piston part 21, a screw nut 22, a cum member 23, a screw rod 24, a spring member 25, a stopper member 26, a push rod 27 and an end plug 28, and assumed is a mechanism in which the rotating member 12 is rotated by a hand or the like to thereby push out a suited amount of the eyeliner liquid cosmetic filled directly into the storing part 11 toward the coating mechanism 30 at a front part.

The coating mechanism 30 is constituted from a holder member 31 mounted at a front part of the main body part 10, a brush 32 which is a coating part mounted on the holder member 31, a pipe member 33, a pipe connecter 34, a sealing ball 35 and a sealing ball holder 36.

The cap mechanism 40 is engaged detachably with the holder member 31, and it is a cap body for preventing the brush 32 which is a coating part from being dried and has internally an inner cap body 42 which is extensible by a spring member 41. Reference number 45 shown in the drawing is a small-sized stirrer (stirring ball made of SUS) which can evenly stir the water based liquid makeup cosmetic filled, and reference number 46 is a safety tab.

In the eyeliner A, the rotating member 12 is rotated by a hand or the like to allow the piston part 21 to transfer forward, and a suited amount of the eyeliner cosmetic liquid filled in the storing part 11 passes through the pipe member 33 to penetrate into the brush 32. The brush 32 is filled with the eyeliner liquid cosmetic, and it is coated on a periphery of eyes.

In the water based liquid makeup cosmetic of the present invention, though the tabular pigment which forms tabular coarse particles is used as described above, the tabular coarse particles are less liable to be settled down, and even when they have been settled down, the cosmetic can evenly be redispersed by slight force. Accordingly, assumed is a structure in which the cosmetic can be stored directly in the storing part 11 for a cosmetic in the eyeliner A shown in FIG. 1.

EXAMPLES

Next, the present invention shall be explained in further details with reference to examples and comparative examples, but the present invention shall by no means be restricted to the following examples.

Examples 1 to 5 and Comparative Examples 1 to 6

Blend components (prescribed amounts of a tabular pigment, a dispersant, a spherical powder, a thickener, a coating film-forming agent emulsion and water and, if necessary, optional blend components such as a surfactant, a pH controlling agent, an antiseptic agent, a moisturizing agent, a chelating agent and the like) in a formation shown in the following Table 1 and Table 2 were put in a dispersing machine by an optional amount and dispersed to thereby prepare the respective water based liquid makeup cosmetics.

The respective water based liquid makeup cosmetics thus obtained were evaluated for a fixing property, redispersibility and a coating property by the following evaluation methods. The fixing property and the coating property were evaluated by means of a cosmetic applicator (eyeliner) having a constitution shown below.

The results thereof are shown in the following Table 1.

Constitution of Cosmetic Applicator (Eyeliner):

The respective water based liquid makeup cosmetics obtained by the preparing method described above were filled into the eyeliner shown in FIG. 1 to evaluate the fixing property and the coating property, wherein the brush 32 which is a coating part is installed at a tip part of the eyeliner; the rotating member 12 provided at the rear end part of the pen type container is rotated to thereby allow the piston part 21 in the container 11 to go forward; and a fixed amount of the content liquid is discharged into the brush 32.

Evaluation Method of Fixing Property:

The fixing property was evaluated by coating the eyeliner cosmetic on an inner arm of a test subject (female panelist) in a form of a line having a length of 10 cm by means of an eyeliner, leaving the coated cosmetic standing for 20 minutes, then applying a warm water stream of 35° C. onto the coated part and rubbing lightly the coated part with a palm to visually evaluate the state of the eyeliner cosmetic remaining on the skin according to the following evaluation criteria.

Evaluation Criteria:

◎: No change was visually observed before and after washing with warm water

○: Scarce change was visually observed before and after washing with warm water

Δ: Coated line partly disappeared or faded away x: Drawn line of the cosmetic coated on the skin completely disappeared Evaluating Method of Redispersibility:

The water based liquid makeup cosmetic was put in a screw capped test tube (inner volume: 7 ml), and a stirring ball (made of SUS, diameter: 4 mm) for stirring a content was put therein. The test tube was sealed tightly and left standing still at 50° C. for one month, and then it was shaken by a hand to observe the movement of the stirring ball, whereby the redispersibility was evaluated according to the following evaluation criteria.

Evaluation Criteria:

○: Stirring ball was moved by shaking one to two times

Δ: Stirring ball was moved by shaking three to nine times x: Stirring ball was not moved without shaking ten or more times Evaluating Method of Coating Property:

An eyeliner filled the water based liquid makeup cosmetic in a container thereof was used to draw five lines having a width of 1 to 2 mm and a length of 5 cm on the back of a hand, and the coating property was evaluated based on drawing feeling in drawing the lines and intensity of the drawn lines according to the following evaluation criteria.

Evaluation Criteria:

○: Good (lines are liable to be drawn and have a satisfactory intensity)

Δ: Average (a little starving and feathering were observed, and no practical problems are involved therein)

x: Inferior (a lot of starving and feathering was observed, and practical problems are involved therein)

TABLE 1

| | | Example | | | | |
|---|---|---|---|---|---|---|
| Kind of blend compound | Blend compound | 1 | 2 | 3 | 4 | 5 |
| Tabular pigment | Iron oxide · titanium dioxide coated mica*1 | 15 | 15 | 15 | 0 | 0 |
| | Red iron oxide · titanium dioxide coated mica*2 | 0 | 0 | 0 | 15 | 15 |
| Dispersant | Alkyl acrylate copolymer*3 | 0.6 | 3.0 | 4.5 | 3.0 | 4.5 |
| Dispersant (surfactant) | Polyethylene glycol fatty acid ester | 0 | 0 | 0 | 0.3 | 0.5 |
| Dispersant aid (spherical powder) | Polymethyl methacrylate (spherical powder)*4 | 1 | 2 | 4 | 2 | 4 |
| Coating film-forming agent | Alkyl acrylate copolymer emulsion*5 | 20 | 15 | 10 | 15 | 10 |
| | (Solid content) | 9 | 6.75 | 4.5 | 6.75 | 4.5 |
| pH controlling agent | 2-Amino-2-methyl-1-propanol | 0.2 | 0.6 | 0.9 | 0.6 | 0.9 |
| Chelating agent | Disodium edetate | 0.3 | 0.3 | 0.3 | 0.3 | 0.3 |
| Moisturizing agent | 1,3-Butylene glycol | 8 | 8 | 8 | 8 | 8 |
| Thickener | Xanthan gum | 0.3 | 0.25 | 0.5 | 0.5 | 0.6 |
| Antiseptic agent | Methyl paraben | 0.4 | 0.4 | 0.4 | 0.4 | 0.4 |
| Antiseptic agent | Sodium dehydroacetate | 0.1 | 0.1 | 0.1 | 0.1 | 0.1 |
| Purified water | Purified water | balance | balance | balance | balance | balance |
| Total amount (mass %) | | 100 | 100 | 100 | 100 | 100 |
| Performance evaluation of water based liquid makeup cosmetic | | | | | | |
| Viscosity*6 (mPa · s) (Shear rate 76.8 [$s^{-1}$]) | | 91 | 58 | 152 | 136 | 223 |
| Fixing property | | ○ | ◎ | ◎ | ○ | ○ |
| Redispersibility | | ○ | ○ | ○ | ○ | ○ |
| Coating performance | | ○ | ○ | ○ | ○ | ○ |

*1average particle diameter: 20 μm

*2average particle diameter: 50 μm

*3alkyl acrylate copolymer, Luvimer 100P manufactured by BASF AG.

*4average particle diameter: 0.3 μm

*5alkyl acrylate copolymer emulsion: Yodosol GH800 manufactured by Nippon NSC Ltd. (containing a surfactant with a limit set to 2.0 mass %, Examples 1 to 3), COVACRYL MS11 manufactured by Daito Kasei Kogyo Co., Ltd. (soap free, Examples 4 and 5)

*6viscosity measuring conditions: EMD type viscometer manufactured by Tokimec Inc., standard cone rotor 20 rpm, 25° C., share rate: 76.8 [$s^{-1}$]

TABLE 2

| | | Comparative Example | | | | | |
|---|---|---|---|---|---|---|---|
| Kind of blend compound | Blend compound | 1 | 2 | 3 | 4 | 5 | 6 |
| Tabular pigment | Iron oxide · titanium dioxide coated mica*1 | 15 | 15 | 15 | 15 | 0 | 0 |
| | Red iron oxide · titanium dioxide coated mica*2 | 0 | 0 | 0 | 0 | 15 | 15 |
| Dispersant | Alkyl acrylate copolymer*3 | 3.0 | 3.0 | 3.0 | 0.0 | 3.0 | 3.0 |
| Dispersant (surfactant) | Polyethylene glycol fatty acid ester | 0.6 | 1.0 | 0.6 | 0.6 | 0.3 | 0.5 |

TABLE 2-continued

| Kind of blend compound | Blend compound | Comparative Example 1 | 2 | 3 | 4 | 5 | 6 |
|---|---|---|---|---|---|---|---|
| Dispersant aid (spherical powder) | Polymethyl methacrylate (spherical powder)*4 | 0 | 2 | 2 | 2 | 2 | 2 |
| Coating film-forming agent | Alkyl acrylate copolymer emulsion*5 | 20 | 20 | 0 | 10 | 15 | 15 |
| | (Solid content) | 9 | 9 | 0 | 4.5 | 6.75 | 6.75 |
| pH controlling agent | 2-Amino-2-methyl-1-propanol | 0.6 | 0.6 | 0.6 | 0.0 | 0.6 | 0.6 |
| Chelating agent | Disodium edetate | 0.3 | 0.3 | 0.3 | 0.3 | 0.3 | 0.3 |
| Moisturizing agent | 1,3-Butylene glycol | 8 | 8 | 8 | 8 | 8 | 8 |
| Thickener | Xanthan gum | 0.5 | 0.25 | 0.5 | 0.5 | 0.1 | 0.7 |
| Antiseptic agent | Methyl paraben | 0.4 | 0.4 | 0.4 | 0.4 | 0.4 | 0.4 |
| Antiseptic agent | Sodium dehydroacetate | 0.1 | 0.1 | 0.1 | 0.1 | 0.1 | 0.1 |
| Purified water | Purified water | balance | balance | balance | balance | balance | balance |
| Total amount (mass %) | | 100 | 100 | 100 | 100 | 100 | 100 |
| Performance evaluation of water based liquid makeup cosmetic | | | | | | | |
| Viscosity*6 (mPa · s) (Shear rate 76.8 [$s^{-1}$]) | | 136 | 54 | 130 | 130 | 45 | 263 |
| Fixing property | | X | X | X | X | ○ | ○ |
| Redispersibility | | X | Δ | ○ | ○ | Δ | ○ |
| Coating performance | | ○ | ○ | ○ | ○ | Δ | X |

*1average particle diameter: 20 μm
*2average particle diameter: 50 μm
*3alkyl acrylate copolymer, Luvimer 100P manufactured by BASF AG.
*4average particle diameter: 0.3 μm
*5alkyl acrylate copolymer emulsion: Yodosol GH800 manufactured by Nippon NSC Ltd. (containing a surfactant with a limit set to 2.0 mass %, Comparative Examples 1, 2 and 4), COVACRYL MS11 manufactured by Daito Kasei Kogyo Co., Ltd. (soap free, Comparative Examples 5 and 6)
*6viscosity measuring conditions: EMD type viscometer manufactured by Tokimec Inc., standard cone rotor 20 rpm, 25° C., share rate: 76.8 [$s^{-1}$]

As apparent from the results shown in Table 1 and Table 2, it has been found that the water based liquid makeup cosmetics prepared in Examples 1 to 5 falling in the scope of the present invention are excellent in a fixing property, redispersibility and a coating property as compared with those prepared in Comparative Examples 1 to 6 falling outside the scope of the present invention.

INDUSTRIAL APPLICABILITY

Provided by the present invention is a water based liquid makeup cosmetic containing a tabular pigment, wherein it is liable to draw fine lines and is excellent in a water resistant fixing performance; tabular coarse particles contained therein as an active ingredient are less liable to settle down; and the cosmetic is evenly redispersed by slightly shaking even when it is not used for a while. In addition thereto, the cosmetic makes it possible to provide makeup imparted with brilliance since it contains the pigment described above, and therefore it has high industrial applicability.

What is claimed is:

1. A water based liquid eye-makeup cosmetic having a viscosity of 50 to 250 mPa·s and consisting of at least a tabular pigment, a pigment dispersant, a coating film-forming agent, 0.001 to 0.5 mass % of a surfactant, a neutralizing agent, water a chelating agent, a moisturizing agent, a thickener, an antiseptic agent, and a spherical powder, wherein the pigment dispersant is a copolymer which is prepared from raw material monomers of methacrylic acid, tert-butyl acrylate and ethyl acrylate and which has an acid residue as a side chain in a repetitive structure thereof and is dissolved in water by neutralization, and wherein the coating film-forming agent is an emulsion of a homopolymer or a copolymer prepared from at least one monomer selected from the group consisting of acrylic acid, methacrylic acid and alkyl (C1 to C4 and C8) esters thereof, and wherein the eye-makeup cosmetic is for make up around eyes.

2. The water based liquid eye-makeup cosmetic according to claim 1, wherein the tabular pigment is at least one pigment selected from the group consisting of mica, titanium dioxide coated mica, a metal or metal oxide-coated glass flake, an aluminum-coated polyester film and an aluminum powder pigment.

3. The water based liquid eye-makeup cosmetic according to claim 1, wherein the spherical powder is a spherical powder comprising at least one of spherical silica particles, spherical mica particles, spherical nylon particles, spherical acrylic resin particles and spherical polystyrene particles.

4. An eyeliner prepared by filling the water based liquid eye-makeup cosmetic according to claim 1 directly into a storing part of an applicator for a liquid cosmetic equipped with a brush-like coating part.

5. The eyeliner according to claim 4, wherein at least one stirrer is accommodated in the storing part of the applicator for a liquid cosmetic.

* * * * *